US012767622B2

(12) United States Patent
Jang et al.

(10) Patent No.: US 12,767,622 B2
(45) Date of Patent: Oct. 20, 2026

(54) METHOD FOR CHLORINATING AROMATIC COMPOUND

(71) Applicant: HANWHA SOLUTIONS CORPORATION, Seoul (KR)

(72) Inventors: Namjin Jang, Daejeon (KR); Ji Hye Choi, Daejeon (KR); Jinho Park, Daejeon (KR)

(73) Assignee: HANWHA SOLUTIONS CORPORATION, Seoul (KR)

( * ) Notice: Subject to any disclaimer, the term of this patent is extended or adjusted under 35 U.S.C. 154(b) by 654 days.

(21) Appl. No.: 18/262,586

(22) PCT Filed: Jan. 25, 2022

(86) PCT No.: PCT/KR2022/001268
§ 371 (c)(1),
(2) Date: Jul. 24, 2023

(87) PCT Pub. No.: WO2022/158937
PCT Pub. Date: Jul. 28, 2022

(65) Prior Publication Data

US 2024/0092712 A1 Mar. 21, 2024

(30) Foreign Application Priority Data

Jan. 25, 2021 (KR) ........................ 10-2021-0010151

(51) Int. Cl.
*C07C 25/02* (2006.01)

(52) U.S. Cl.
CPC .................................... *C07C 25/02* (2013.01)

(58) Field of Classification Search
CPC ........... C07C 25/02; C07C 17/12; C07C 7/20; C07C 15/06
See application file for complete search history.

(56) References Cited

FOREIGN PATENT DOCUMENTS

| | | | |
|---|---|---|---|
| CN | 109970507 | A | 7/2019 |
| JP | 2006160611 | A | 6/2006 |
| JP | 2010120934 | A | 6/2010 |
| JP | 5658865 | B2 | 1/2015 |
| JP | 5669362 | B2 | 2/2015 |
| KR | 20160069830 | A | 6/2016 |
| KR | 20160107102 | A | 9/2016 |
| KR | 101759512 | B1 | 7/2017 |

OTHER PUBLICATIONS

Jin et al (Kr 101759512 B1 machine translation), 2017.*
European Search Report dated Dec. 13, 2024.

* cited by examiner

*Primary Examiner* — Jafar F Parsa
(74) *Attorney, Agent, or Firm* — Harvest IP Law, LLP

(57) ABSTRACT

The present invention relates to a method for chlorinating an aromatic compound and, more specifically, to a method for chlorinating an aromatic compound to prevent the phenomenon of decreased responsiveness due to foam generation, and to prevent counterflow of a fluid.

By means of the method for chlorinating an aromatic compound according to the present invention, a plurality of column-type reactors are connected in series so that reaction products produced in a former reactor are inserted to a latter reactor, and chlorine gas is inserted in equal measure at the bottom of each reactor. Accordingly, a chlorination reaction occurs in each of the reactors, and hydrogen chloride gas generated in each of the reactors is exhausted from each of the reactors.

15 Claims, 1 Drawing Sheet

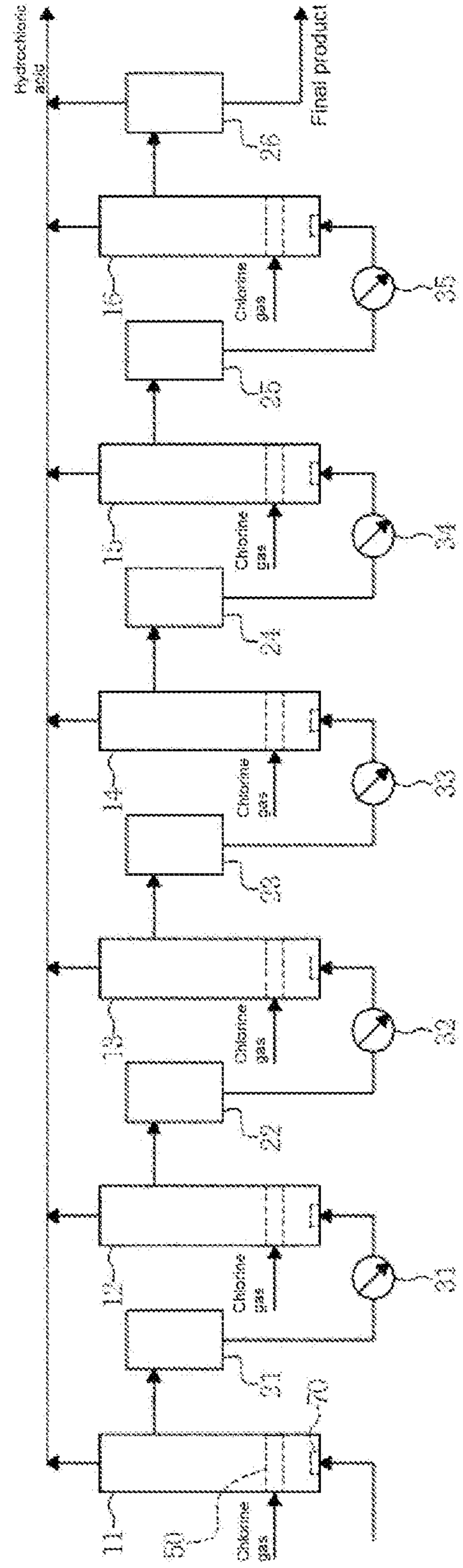
Hydrochloric acid
Final product
26
16
Chlorine gas
35
25
15
Chlorine gas
34
24
14
Chlorine gas
33
23
13
Chlorine gas
32
22
12
Chlorine gas
31
21
70
11
50
Chlorine gas

METHOD FOR CHLORINATING AROMATIC COMPOUND

CROSS-REFERENCE TO RELATED APPLICATION(S)

This application is a National Stage of International Application No. PCT/KR2022/001268 filed on Jan. 25, 2022, claiming priority based on Korean Patent Application No. 10-2021-0010151 filed on Jan. 25, 2021, the disclosure of which is incorporated herein by reference in its entirety.

TECHNICAL FIELD

The present invention relates to a method for chlorinating an aromatic compound, and more specifically, to a method for chlorinating an aromatic compound, which may prevent a reactivity decrease phenomenon caused by foaming and prevent counterflow of a fluid.

BACKGROUND ART

Chlorobenzene or chlorotoluene is a material used in various industrial fields, and is formed by a chlorination reaction of an aromatic compound such as benzene and toluene. As a specific example, monochlorotoluene such as o-chlorotoluene and p-chlorotoluene may be prepared by reacting toluene and chlorine in the presence of a catalyst such as $FeCl_3$. Specifically, when toluene and chlorine are reacted in the presence of a catalyst, a chlorine atom is substituted to produce monochlorotoluene such as o-chlorotoluene and p-chlorotoluene.

Conventionally, when an aromatic compound is chlorinated to prepare chlorobenzene or chlorotoluene as described above, overchlorinated by-products such as dichlorobenzene or dichlorotoluene may be produced depending on a supply ratio of the aromatic compound and the chlorine gas. In order to suppress the production of the by-product as much as possible, in the common production method, benzene or toluene is used in an excessive amount as compared with chlorine, and a large amount of unreacted benzene or toluene, which is mixed with the product after the reaction, is recovered and used again as a reactant.

However, like the common production method, by-products such as dichlorobenzene or dichlorotoluene are produced in a significant amount even with the use of a large amount of benzene or toluene as compared with chlorine, and thus, selectivity and yield are not increased beyond a certain level.

In order to solve the problem of the prior art as such, in Korean Patent Registration No. 10-1759512 which was previously filed by the present applicant, toluene and chlorine are reacted in one reactor having a multistage structure including a reaction unit and a cooling unit to improve the selectivity of chlorotoluene and p-chlorotoluene, thereby increasing the reaction yield.

However, in the reactor having a multistage structure, as the chlorination reaction occurs, a gas ratio is increased over time, and a residence time of a chlorine gas is decreased toward the upper portion and it is difficult to control a linear velocity of gas in a reactor. Specifically, as a reaction time elapses, the linear velocity of gas in the reactor is increased, and above a certain linear velocity, foam is produced to decrease reactivity and rather decrease a yield.

Thus, the present inventors studied in depth an efficient method of increasing a product yield by maintaining high reactivity even when a chlorination reaction time is elapsed.

DISCLOSURE

Technical Problem

An object of the present invention is to provide a method for chlorinating an aromatic compound, which may prevent a reactivity decrease phenomenon caused by foaming and prevent counterflow of a liquid in a reactor.

Technical Solution

In one general aspect, a method for chlorinating an aromatic compound includes: in a plurality of column-type reactors connected in series, introducing a reaction product produced in a former reactor to a latter reactor, introducing a chlorine gas to a low portion of each reactor in the same amount to perform a chlorination reaction in each reactor, and discharging a hydrogen chloride gas produced in each of the reactors from each reactor.

In the method for chlorinating an aromatic compound according to an exemplary embodiment of the present invention, the reaction product produced in the former reactor may be cooled by a heat exchanger disposed between the adjacent reactors and be introduced to the low portion of the latter reactor quantitatively.

In the method for chlorinating an aromatic compound according to an exemplary embodiment of the present invention, the hydrogen chloride gas may be further discharged from the reaction product produced in the former reactor by a buffer drum and then the reaction product may be supplied to the latter reactor.

In the method for chlorinating an aromatic compound according to an exemplary embodiment of the present invention, the chlorine gas may be introduced to the low portion in the reactor through a gas sparger which is disposed in each reactor and has a plurality of holes formed thereon.

In the method for chlorinating an aromatic compound according to an exemplary embodiment of the present invention, a diameter of the hole of the gas sparger may be 1 to 5 mm.

In the method for chlorinating an aromatic compound according to an exemplary embodiment of the present invention, the chlorine gas may be introduced at a linear velocity of 5 to 10 m/sec through the gas sparger hole.

In the method for chlorinating an aromatic compound according to an exemplary embodiment of the present invention, the aromatic compound and the chlorine gas may be introduced at 1:1/16 to 1/8 based on the total moles.

In the method for chlorinating an aromatic compound according to an exemplary embodiment of the present invention, a conversion rate in each reactor may be 1 to 15%.

In the method for chlorinating an aromatic compound according to an exemplary embodiment of the present invention, the aromatic compound is introduced to the low portion in the reactor through a raw material supply nozzle which is disposed in a lower portion than the gas sparger in the reactor, and the aromatic compound may be introduced at a linear velocity of 10 to 40 m/sec through the raw material supply nozzle.

In the method for chlorinating an aromatic compound according to an exemplary embodiment of the present invention, the linear velocity of gas in each reactor may be 7 cm/sec or less.

In the method for chlorinating an aromatic compound according to an exemplary embodiment of the present invention, the reaction product may be cooled to a temperature of 0° C. or higher and 25° C. or by the heat exchanger.

In the method for chlorinating an aromatic compound according to an exemplary embodiment of the present invention, a bubble diameter of the chlorine gas introduced to each reactor may be 0.1 mm or more and 5 mm or less.

In the method for chlorinating an aromatic compound according to an exemplary embodiment of the present invention, the reaction of each reactor may be performed in the presence of a main catalyst and a cocatalyst.

In the method for chlorinating an aromatic compound according to an exemplary embodiment of the present invention, the main catalyst may be at least one selected from the group consisting of $FeCl_3$, ferrocene, $PtO_2$, $SbCl_3$, and Fe.

In the method for chlorinating an aromatic compound according to an exemplary embodiment of the present invention, the cocatalyst may be at least one selected from the group consisting of $S_2Cl_2$, thianthrene, diphenylselenide, tetrachlorophenoxathin, dichlorothiantrene, tetrachlorothiantrene, and polychlorothiantrene.

In the method for chlorinating an aromatic compound according to an exemplary embodiment of the present invention, contents of the main catalyst and the cocatalyst (main catalyst:cocatalyst) may be 1:0.59 or more and 1:0.76 or less, based on a mole ratio.

Advantageous Effects

In the method for reacting an aromatic compound according to the present invention, the same amount of chlorine gas is supplied to a plurality of reactors arranged in series and a reaction product produced in a former reactor is supplied to a latter reactor, thereby preventing foaming and a decrease in chlorination reactivity caused by an increase in gas volume over a reaction time, and thus, increasing a reaction yield of the product to be prepared.

In addition, a conversion rate of the reacted product is improved to decrease formation of wastes such as chlorine as an unreacted reactant and hydrogen chloride (HCl) as a reaction by-product, and thus, an environmentally friendly and economical method for reacting an aromatic compound is provided.

DESCRIPTION OF DRAWINGS

FIG. 1 is an exemplary schematic diagram of a reaction device which is used in a method for chlorinating an aromatic compound according to an exemplary embodiment of the present invention.

BEST MODE

Unless otherwise defined herein, all terms used in the present specification (including technical and scientific terms) may have the meaning that is commonly understood by those skilled in the art. In the entire specification, unless otherwise particularly described, a part "comprising" a constituent element will be understood to imply further inclusion of other constituent elements rather than the exclusion of any other constituent elements. In addition, unless otherwise particularly described, a singular form includes a plural form herein.

The terms "about", "substantially", and the like used in the present specification are used in the meaning of the numerical value or in the meaning close to the numerical value when unique manufacture and material allowable errors are suggested in the mentioned meaning, and are used for preventing the disclosure mentioning a correct or absolute numerical value for better understanding of the present application from being unfairly used by an unconscionable infringer.

In the present specification, the term "combination(s) thereof" included in the expression in a Markush format means a mixture of combination of one or more selected from the group consisting of constituents described in the expression in a Markush format, and means inclusion of one or more selected from the group consisting of the constituents.

Conventionally, when an aromatic compound is chlorinated to prepare chlorobenzene or chlorotoluene, overchlorinated by-products such as dichlorobenzene or dichlorotoluene were produced depending on a supply ratio of the aromatic compound and chlorine gas. Thus, a reaction yield was intended to be increased by reacting toluene and chlorine in one reactor having a multistage structure including a reaction unit and a cooling unit to improve selectivity of o-chlorotoluene and p-chlorotoluene, but since a chlorination reaction occurs in the reactor having a multistage structure, a gas ratio is increased over time, so that a residence time of a chlorine gas is decreased toward the upper portion and it is difficult to control a linear velocity of gas in the reactor. Thus, as the reaction time elapses, a linear velocity exceeds a certain level to cause foam, thereby decreasing a yield.

In the present invention, a plurality of column-type reactors are connected in series so that a reaction product produced in a former reactor is introduced to a latter reactor, chlorine gas is introduced to a low portion of each reactor in the same amount to perform a chlorination reaction in each reactor, and a hydrogen chloride gas produced in each reactor is discharged from each reactor. Thus, foaming and a decrease in chlorination reactivity caused by an increase in gas volume due to the elapse of the reaction time are prevented, thereby increasing a reaction yield of the product to be prepared.

In addition, a conversion rate of the product is improved to decrease occurrence of wastes such as chlorine as an unreacted reactant and hydrogen chloride (HCl) as a reaction by-product, thereby providing an environmentally friendly and economical method for reacting an aromatic compound.

Specifically, in the plurality of reactors arranged in series, a reaction product produced in a foremost reactor which is disposed at the forefront and in which a chlorine gas is first supplied to a raw material including an aromatic compound may be supplied to a latter reactor adjacent thereto, and sequentially, be passed through each reactor to be supplied to a reactor disposed at the last stage.

In each reactor, the chlorine gas is injected into the reaction product produced in a former stage reaction, that is, the raw material including the aromatic compound to produce a product by the chlorination reaction of the aromatic compound and the chorine gas.

In an exemplary embodiment of the present invention, the aromatic compound may be benzene or toluene, and the product may be a chlorinated product thereof, but they are not limited thereto. In a specific example, the chlorine gas may be supplied to toluene which is the aromatic compound to produce o-chlorotoluene and p-chlorotoluene. More specifically, an excessive amount of aromatic compound may be supplied to the inside of each reactor, in which "excessive amount" means, as a specific example, an environment in which toluene is present in an amount greater than a stoichiometric reaction equivalence ratio (1:1) of toluene and chlorine gas which are the reactants of the following Reaction Formula 1. Thus, in the environment, the chlorine gas to be injected may be all reacted with toluene.

The step of supplying the chlorine gas to toluene to produce o-chlorotoluene and p-chlorotoluene may be performed by a reaction represented by the following Reaction Formula 1:

[Reaction Formula 1]

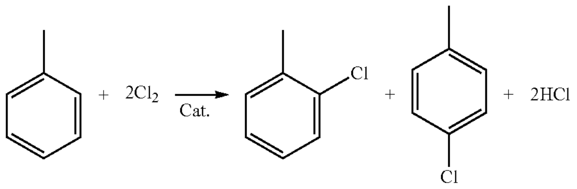

As such, since the hydrogen chloride gas is included in the final product, the chlorination reaction of an aromatic compound of the present invention has an increased gas ratio as the reaction proceeds, and foam may occur as the linear velocity of gas in the reactor is increased. Thus, the yield of the final product may be affected.

In the present invention, since the hydrogen chloride gas produced in each reactor is discharged to the upper portion, when the reaction product is supplied from the former reactor to the latter stage, the hydrogen chloride gas is removed from the reaction product. In addition to the hydrogen chloride gas, unreacted chlorine gas may be discharged, of course.

The present invention as such may prevent foaming caused by a linear velocity increase of gas due to an increase in gas volume in the reactor as the reaction time elapses, and since the constant linear velocity of gas in each reactor may be maintained, it is easy to control the linear velocity and it may be advantageous to design a production preparation process and maintain the process. Furthermore, occurrence of counterflow when a liquid such as a raw material is supplied due to an increase in gas volume inside the reactor may be prevented.

In an exemplary embodiment of the present invention, a reaction product produced in the former reactor by a buffer drum disposed between adjacent reactors may be supplied to the latter reactor after further discharging a hydrogen chloride gas. As the buffer drum, a buffer drum which is used in removing hydrogen chloride gas in the art may be applied, and an accommodation space which may accommodate the reaction product from which the hydrogen chloride gas has been first discharged in the former reactor is formed, and the hydrogen chloride gas is secondarily discharged to remove the hydrogen chloride gas included in the reaction product as much as possible. In the buffer drum, the reaction product from which the hydrogen chloride gas is secondarily removed may be supplied to the latter reactor. As such, when the reaction product in the former reactor is supplied through the buffer drum to the latter reactor, the hydrogen chloride gas in the reaction product may be secondarily removed, and thus, a high-purity product may be produced and also the linear velocity of the gas in the reactor may be more easily adjusted.

Meanwhile, since the reaction between the aromatic compound and the chlorine gas is exothermic, the temperature of the reaction solution is raised as the reaction proceeds. Thus, as the more chlorine gas is introduced to excessive toluene, the more the reaction proceeds and the higher the temperature of the reaction solution rises. Since the selectivity of the chlorinated reaction product of the aromatic compound such as o-chlorotoluene and p-chlorotoluene tends to be decreased as the reaction temperature rises, the selectivity may be decreased when the reaction proceeds too much.

Thus, in an exemplary embodiment of the present invention, the reaction product produced in the former reactor may be cooled by the heat exchanger disposed between adjacent reactors and introduced to the low portion of the latter reactor quantitatively. The cooling may be performed at a temperature of 0° C. or higher and about 50° C. or lower, specifically 5° C. or higher and 30° C. or lower, but the cooling may proceed without limitation as long as chlorine is not liquefied. Specifically, depending on the supply pressure of the chlorine gas, the temperature may be 25° C. at 7.81 bara, and when the supply pressure of chlorine is 5.07 bara, the temperature may be 10° C. When the supply pressure of the chlorine gas is 3.7 bara, the cooling may be performed to 0° C. However, in order to lower the temperature of the chlorine gas, a refrigerant at a temperature lower than the temperature to perform the cooling is needed, and cooling more than needed causes excessive investment. Therefore, considering chlorine liquefaction temperature, operating cost, and the like depending on operating pressure, the above range may be preferred. However, the present invention is not limited thereto.

In an exemplary embodiment of the present invention, the injection of the chlorine gas may be performed through a gas sparger which is disposed in each reactor and has a plurality of holes formed thereon. Specifically, the gas sparger is disposed in the low portion inside the reactor and introduces the chlorine gas to the low portion inside the reactor. The gas sparger is not limited and any gas sparger may be applied as long as it is used in the art. A diameter of the hole (nozzle) of the gas sparger from which the chlorine gas is sprayed may be 0.5 mm to 5 mm, specifically 1 to 3 mm, but is not limited thereto. However, the linear velocity of the chlorine gas may be easily set in the range.

The chlorine gas may be supplied in the same amount in each reactor, and may be introduced (injected) at a linear velocity in the gas sparger hole of 1 to 20 m/sec, specifically 5 to 10 m/sec through the gas sparger. Since the chlorine gas is injected at the linear velocity as such, the linear velocity of 1 to 7 cm/sec may be shown in the reactor, and the linear velocity is lowered toward the upper portion in the column-type reactor, thereby solving the problems of a decrease in a reaction rate and foaming due to agglomeration of gas particles.

The amount of the chlorine gas in the reactor may be less than 1/8, based on the total moles of excessive toluene in the raw material (reaction solution) including the aromatic compound. More specifically, it may be more than 1/16 and less than 1/8 or 1/14 or more and 1/10 or less, but is not limited thereto. However, by introducing the chlorine gas in the above range, the reaction between toluene and chlorine may be performed with a high selectivity throughout the process.

A bubble diameter of the chlorine gas to be injected may be 0.1 mm or more and 5 mm or less. It is preferred that the chlorine gas to be injected into the reaction solution has a uniform size distribution. When the bubble of the chlorine gas is too small, the reactivity of a side reaction product may be increased to decrease the selectivity. When the bubble diameter of the chlorine gas is too large, the reactivity of the chlorine gas is decreased so that the size of the reactor should be large, and thus, process costs such as investment and operating costs may be unnecessarily increased.

In an exemplary embodiment of the present invention, the injection of the aromatic compound may be performed through a raw material supply nozzle disposed in the lower portion than the gas sparger in each reactor. The raw material including the aromatic compound may be supplied to the lower portion than the chlorine gas inside the reactor through the raw material supply nozzle disposed in the lower portion than the gas sparger. A diameter of the hole (nozzle) of the raw material supply nozzle from which the aromatic compound is sprayed may be 1 mm to 9 mm, specifically 1 to 5 mm, but is not limited thereto. The aromatic compound may be introduced at a linear velocity of 10 to 60 m/sec, specifically 10 to 40 m/sec through the raw material supply nozzle, but is not limited thereto. However, within the range, the linear velocity of a liquid may be shown in the reactor described later.

In the reactor, an average liquid linear velocity may be 0.1 cm/s or more and 100 cm/s or less. Within the range, the residence time of the reactant in the reactor is adjusted, so that excellent reactivity may be shown.

Specifically, as a method for increasing the liquid linear velocity inside the reactor for effective heat removal (cooling), when the flow inside the reactor is improved, back mixing occurs by counterflow to lower the selectivity. In addition, when the linear velocity of the chlorine gas is increased by the increase in a liquid linear velocity, the conversion rate of the chlorine gas is less than 100%, and the consumed amount of chlorine gas is increased. When the conversion rate of chlorine is low, it is difficult to separate the hydrogen chloride gas and the chlorine gas which are reaction products, and thus, the chlorine gas is treated as a large amount of wastes.

Since the aromatic compound and the chlorine gas are supplied in the above ranges, in the present invention, gases in the reactor have constant linear velocities, and a decrease in selectivity and waste of chlorine gas due to the back mixing may be prevented. Specifically, the linear velocity of gas inside each reactor may be 10 cm/sec or less, more specifically 4 cm/sec or less. Since foaming is significantly suppressed in the range, the product may be produced at a high yield. Herein, the gas may include hydrogen chloride gas produced by the reaction as well as chlorine gas in the reactor.

In an exemplary embodiment of the present invention, the chlorine gas may be introduced at 5 to 10 L/min, based on the aromatic compound introduced at 650 g/min in the reactor having an inner diameter of 13 cm and a height of 600 cm. The conversion rate in each reactor is 1 to 15% in the range, and an excellent conversion rate may be shown.

In an exemplary embodiment of the present invention, the reaction may be performed in the presence of a main catalyst and a cocatalyst. Specifically, the main catalyst may be one or more selected from the group consisting of $FeCl_3$, ferrocene, $PtO_2$, $SbCl_3$, and Fe. The cocatalyst may be one or more selected from the group consisting of $S_2Cl_2$, thianthrene, diphenylselenide, tetrachlorophenoxathin, dichlorothiantrene, tetrachlorothiantrene, and polychlorothiantrene.

In addition, contents of the main catalyst and the cocatalyst (main catalyst:cocatalyst) may be 1:0.59 or more and 1:0.76 or less, based on a mole ratio. This is the condition to improve the selectivities of o-chlorotoluene and p-chlorotoluene to about 99.5% or more, as recognized by referring Korean Patent Appln. No. 10-2016-0069830 which is the preceding invention of the present inventors.

Though the contents of the main catalyst and the cocatalyst of the present invention are not limited to the range, when the technology is applied to the present invention, the effect of improving selectivity may be further improved.

In the chlorination method according to an exemplary embodiment of the present invention, the product may be separated and recovered after the reaction is completed in the last reactor. In addition to the product to be desired, an unreacted aromatic compound, excessive chlorinated by-products, the main catalyst, and the cocatalyst remain by the reaction of the aromatic compound and the chlorine gas, and thus, separation for reuse thereof is required. Various methods known in the art may be adopted for the separation.

Hereinafter, a specific example of performing the reaction method according to an exemplary embodiment of the present invention will be described as the case performed in a plurality of reactors connected in series, referring to FIG. 1.

First, six identical column-type reactors are arranged in a row parallel to the ground, and a buffer drum and a heat exchanger are disposed, respectively, between the reactors. Herein, as illustrated in the drawing, the buffer drum may be further provided in the latter stage of the last reactor.

Further, a gas sparger disposed in the reactor disposed in the forefront stage and a raw material including a chlorine gas and an excessive amount of aromatic compound through a raw material supply nozzle are introduced, respectively.

The chlorination method of the present invention may be performed by the chlorination reaction in each reactor, sequentially through the reactors from the foremost reactor to the last reactor.

Hereinafter, description will be provided assuming that a reactor disposed in the forefront stage is referred to as a first reactor 11, a reactor disposed in the latter stage adjacent thereto is referred to as a second reactor 12, reactors disposed in the latter stages adjacent thereto are sequentially referred to as first to sixth reactors 11, 12, 13, 14, 15, and 16, to the last stage, and in this manner, buffer drums are referred to as first to sixth buffer drums 21, 22, 23, 24, 25, and 16 and heat exchangers are referred to as first to fifth heat exchangers 31, 32, 33, 34, and 35.

A reaction product produced in the first reactor 11 may be subjected to a first removal of hydrogen chloride gas from the first reactor 11, followed by a second removal of hydrogen chloride gas through the first buffer drum 21. Thereafter, it may be supplied to the first heat exchanger 31, cooled through the first heat exchanger 31, and supplied to the second reactor 12. In this manner, it may be passed through the second to fifth reactors 12, 13, 14, and 15, the second to fifth buffer drums 22, 23, 24, and 25, and the second to fifth heat exchangers 32, 33, 34, and 35, and finally supplied to the sixth reactor 16. The reaction product which finally completed the reaction in the sixth reactor 16 may be passed through the sixth buffer drum 26 to remove hydrogen chloride.

To the first to sixth reactors 11, 12, 13, 14, 15, and 16, each chlorine gas is identically supplied, and in each reactor, the introduced chlorine gas and the raw material including the aromatic compound or the reaction produce supplied from the former reactor are reacted to produce a chlorinated product. The reaction product supplied to each reactor is passed through the first to fifth heat exchangers 31, 32, 33, 34, and 35 to be cooled to 0° C. or higher and 25° C. or lower. The reason for cooling to the temperature range is as described above.

Hereinafter, the preferred examples and the comparative examples of the present invention will be described. However, the following examples are only a preferred exemplary embodiment of the present invention, and the present invention is not limited thereto.

Example 1

Toluene and a chlorine gas were introduced into a reactor having an inner diameter of 13 cm and a height of 600 cm, in which the linear velocity of gas in the reactor was adjusted by adjusting the chlorine gas to be introduced at a linear velocity of 5 to 10 m/sec through a gas sparger hole and the raw material including toluene to be introduced at 10 to 40 m/sec through a raw material supply nozzle. At this time, a mole ratio between toluene and chlorine was 2:1, $FeCl_3$ was used as a catalyst, $S_2Cl_2$ was used as a cocatalyst, and concentrations of $F_3Cl_3$ and $S_2Cl_2$ were 300 ppm and 150 ppm, respectively.

Thereafter, a gas-hold up which is a gas volume fraction in the total volume of gas-liquid phase was measured, a surface area was measured by the bubble size and the gas-hold up in the reactor, and it was determined whether foam was formed, for the reactor. The size of a chlorine bubble in the nozzle of the sparger was injected as 2 mm. The results are shown in the following Table 1.

TABLE 1

| Linear velocity (cm/sec) | Gas-hold up | Surface area per unit volume ($m^2/m^3$) |
|---|---|---|
| 1 | 0.041 | 120 |
| 2 | 0.085 | 254 |
| 3 | 0.131 | 393 |
| 4 | 0.179 | 536 |
| 5 | 0.227 | 682 |
| 6 | 0.227 | 831 |
| 7 | 0.327 | 981 |

Referring to Table 1, it was confirmed that foam was hardly formed at a linear velocity of 4 or less.

Example 2

To a reactor having an inner diameter of 13 cm and a height of 600 cm, toluene was introduced at 650 g/min and a chlorine gas was introduced at 5 L/min. Chlorine was supplied at 7 m/sec through a gas sparger hole and toluene was supplied at 20 m/sec through a liquid sparger hole.

The linear velocity of gas in the reactor was 1.77 cm/sec.

At this time, a toluene conversion rate was calculated by the following Calculation Formula 1:

$$\text{Toluene conversion rate}=(\text{supply amount}-\text{toluene after reaction})/\text{supply amount} \quad \text{(Calculation Formula 1)}$$

In Example 2, the toluene conversion rate was confirmed to be 2.7% which is the theoretical conversion rate. Accordingly, it was confirmed that it is very easy to design a chlorination reaction in the present invention.

Hereinabove, although the present invention has been described by specific matters, exemplary embodiments, and drawings, they have been provided only for assisting in the entire understanding of the present invention. Therefore, the present invention is not limited to the exemplary embodiments. Various modifications and changes may be made by those skilled in the art to which the present invention pertains from this description.

Therefore, the spirit of the present invention should not be limited to the above-described exemplary embodiments, and the following claims as well as all modified equally or equivalently to the claims are intended to fall within the scope and spirit of the invention.

The invention claimed is:

1. A method for chlorinating an aromatic compound, the method comprising:

in a plurality column-type reactors connected in series, introducing a reaction product produced in a former reactor to a latter reactor, introducing a chlorine gas to a low portion of each reactor in the same amount to perform a chlorination reaction in each reactor, and discharging a hydrogen chloride gas produced in each of the reactors from each reactor, wherein the aromatic compound and the chlorine gas are introduced at 1:1/16 to 1/8 based on the total moles.

2. The method for chlorinating an aromatic compound of claim 1, wherein the reaction product produced in the former reactor is cooled by a heat exchanger disposed between the adjacent reactors and introduced to a low portion of the latter reactor quantitatively.

3. The method for chlorinating an aromatic compound of claim 1, wherein the hydrogen chloride gas is further discharged from the reaction product produced in the former reactor by a buffer drum disposed between the adjacent reactors and then the reaction product is supplied to the latter reactor.

4. The method for chlorinating an aromatic compound of claim 1, wherein the chlorine gas is introduced to a low portion in the reactor through a gas sparger which is disposed in each reactor and has a plurality of holes formed thereon.

5. The method for chlorinating an aromatic compound of claim 4, wherein a diameter of the hole of the gas sparger is 1 to 5 mm.

6. The method for chlorinating an aromatic compound of claim 1, wherein the chlorine gas is introduced at a linear velocity of 5 to 10 m/sec through the gas sparger hole.

7. The method for chlorinating an aromatic compound of claim 1, wherein a conversion rate in each reactor is 1 to 15%.

8. The method for chlorinating an aromatic compound of claim 4, wherein the aromatic compound is introduced to the lower portion of the reactor through a liquid sparger which is disposed in a lower portion than the gas sparger in the reactor and has a plurality of holes of raw material supply nozzle formed thereon, and the aromatic compound is introduced at a linear velocity of 10 to 40 m/sec through the raw material supply nozzle.

9. The method for chlorinating an aromatic compound of claim 1, wherein the linear velocity of gas in each reactor is 47 cm/se or less.

10. The method for chlorinating an aromatic compound of claim 2, wherein the reaction product is cooled to a temperature of 0° C. or higher and 25° C. or lower by the heat exchanger.

11. The method for chlorinating an aromatic compound of claim 9, wherein a bubble diameter of the chlorine gas introduced to each of the reactors is 0.1 mm or more and 5 mm or less.

12. The method for chlorinating an aromatic compound of claim 1, wherein the reaction of each of the reactors is performed in the presence of a main catalyst and a cocatalyst.

13. The method for chlorinating an aromatic compound of claim 12, wherein the main catalyst is at least one selected from the group consisting of $FeCl_3$, ferrocene, $PtO_2$, $SbCl_3$, and Fe.

14. The method for chlorinating an aromatic compound of claim 12, wherein the cocatalyst is at least one selected from the group consisting of $S_2Cl_2$, thianthrene, diphenylselenide, tetrachlorophenoxathin, dichlorothiantrene, tetrachlorothiantrene, and polychlorothiantrene.

15. The method for chlorinating an aromatic compound of claim 12, wherein contents of the main catalyst and the cocatalyst (main catalyst:cocatalyst) is 1:0.59 or more and 1:0.76 or less based on a mole ratio.

* * * * *